(12) United States Patent
Hakozaki et al.

(10) Patent No.: US 11,622,963 B2
(45) Date of Patent: Apr. 11, 2023

(54) METHOD OF TREATING A SKIN CONDITION

(71) Applicant: The Procter & Gamble Company, Cincinnati, OH (US)

(72) Inventors: Tomohiro Hakozaki, Cincinnati, OH (US); Leo Timothy Laughlin, II, Mason, OH (US); Jason Martin Winget, Mason, OH (US); Teresa DiColandrea, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 36 days.

(21) Appl. No.: 16/460,308

(22) Filed: Jul. 2, 2019

(65) Prior Publication Data

US 2020/0009123 A1    Jan. 9, 2020

Related U.S. Application Data

(60) Provisional application No. 62/693,613, filed on Jul. 3, 2018.

(51) Int. Cl.
    *A61K 31/455* (2006.01)
    *A61P 17/06* (2006.01)
    *A61K 45/06* (2006.01)

(52) U.S. Cl.
    CPC ............ *A61K 31/455* (2013.01); *A61K 45/06* (2013.01); *A61P 17/06* (2018.01)

(58) Field of Classification Search
    CPC ........ A61K 31/455; A61K 45/08; A61P 17/06
    See application file for complete search history.

(56) References Cited

U.S. PATENT DOCUMENTS

| | | |
|---|---|---|
| 3,755,560 A | 8/1973 | Dickert et al. |
| 3,856,941 A | 12/1974 | Turner |
| 3,859,436 A | 1/1975 | Jacobi |
| 3,867,549 A | 2/1975 | Costello |
| 3,892,853 A | 7/1975 | Cobble |
| 4,007,266 A | 2/1977 | Choay |
| 4,178,372 A | 12/1979 | Coats |
| 4,406,884 A | 9/1983 | Fawzi |
| 4,421,769 A | 12/1983 | Dixon et al. |
| 4,481,187 A | 11/1984 | Kondo |
| 4,485,091 A | 11/1984 | Fitton |
| 4,792,443 A | 12/1988 | Filomeno |
| 4,879,107 A | 11/1989 | Vanlerberghe |
| 4,923,977 A | 5/1990 | Lang |
| 5,053,230 A | 10/1991 | Gazzani |
| 5,140,043 A | 8/1992 | Darr |
| 5,229,104 A | 7/1993 | Sottery |
| 5,302,376 A | 4/1994 | Forestier |
| 5,346,694 A | 9/1994 | Juneja |
| 5,419,896 A | 5/1995 | Bimczok |
| 5,429,815 A | 7/1995 | Faryniarz |
| 5,496,538 A | 3/1996 | Zimmerman |
| 5,520,918 A | 5/1996 | Smith |
| 5,549,886 A | 8/1996 | Grollier |
| 5,549,888 A | 8/1996 | Venkateswaran |
| 5,567,427 A | 10/1996 | Papadakis |
| 5,607,921 A | 3/1997 | Bernard |
| 5,616,332 A | 4/1997 | Herstein |
| 5,629,004 A | 5/1997 | Candau |
| 5,654,341 A | 8/1997 | Struewing |
| 5,707,635 A | 1/1998 | Deckner |
| 5,718,906 A | 2/1998 | Martin |
| 5,718,908 A | 2/1998 | Fanelli |
| 5,736,128 A | 4/1998 | Chaudhuri |
| 5,759,558 A | 6/1998 | Epstein |
| 5,824,666 A | 10/1998 | Deckner |
| 5,833,998 A | 11/1998 | Biedermann et al. |
| 5,871,764 A | 2/1999 | Diaz |
| 5,872,112 A | 2/1999 | Blank |
| 5,876,736 A | 3/1999 | Cohen |
| 5,939,082 A | 8/1999 | Oblong et al. |
| 5,961,999 A | 10/1999 | Bimczok |
| 5,968,528 A | 10/1999 | Deckner et al. |
| 5,972,359 A | 10/1999 | Sine et al. |
| 5,989,536 A | 11/1999 | Deckner |
| 5,993,832 A | 11/1999 | Lorant |
| 6,001,379 A | 12/1999 | Griat |
| 6,042,813 A | 3/2000 | Fowler |
| 6,045,779 A | 4/2000 | Mueller |

(Continued)

FOREIGN PATENT DOCUMENTS

| | | |
|---|---|---|
| AU | 2005293830 B2 | 10/2010 |
| AU | 2016206278 A1 | 2/2017 |

(Continued)

OTHER PUBLICATIONS

Topical 6-Aminonicotinamide plus Oral Niacinamide for the Treatment of Psoriasis, Arch Dermatol Nov. 1978: 114 (11) 632.8, Zackheim.*
All Office Actions, U.S. Appl. No. 16/010,944.
All Office Actions, U.S. Appl. No. 16/015,502.
All Office Actions, U.S. Appl. No. 16/860,837.
Bissett et al., Topical niacinamide reduces yellowing, wrinkling, red blotchiness, and hyperpigmented spots in aging facial skin, International Journal of Cosmetic Science, 2004, vol. 26, pp. 231-238.
Eisele et al., The partial compositional characteristics of apple juice from 175 apple varieties, Journal of Food Composition and Analysis, vol. 18, No. 2-3, Mar. 1, 2005, pp. 213-221.

(Continued)

*Primary Examiner* — Ali Soroush

(74) *Attorney, Agent, or Firm* — Alexandra S. Anoff

(57) ABSTRACT

An improved method of treating a skin barrier condition is disclosed. The method involves identifying a target portion of skin on a person where treatment is desired and applying a low-pH composition to the target portion of skin. The low-pH composition contains an effective amount of a vitamin $B_3$ compound and has a pH of less than 5.0.

12 Claims, 1 Drawing Sheet
Specification includes a Sequence Listing.

(56) References Cited

U.S. PATENT DOCUMENTS

| | | |
|---|---|---|
| 6,099,825 A | 8/2000 | Mcshane |
| 6,153,176 A | 11/2000 | Kaleta |
| 6,174,533 B1 | 1/2001 | SaNogueira, Jr. et al. |
| 6,217,887 B1 | 4/2001 | Beerse |
| 6,218,347 B1 | 4/2001 | Rau |
| 6,224,888 B1 | 5/2001 | Vatter et al. |
| 6,238,678 B1 | 5/2001 | Oblong et al. |
| 6,261,541 B1 | 7/2001 | Karpov |
| 6,281,203 B1 | 8/2001 | Touzan |
| 6,287,582 B1 | 9/2001 | Gott |
| 6,287,583 B1 | 9/2001 | Warren |
| 6,299,885 B1 | 10/2001 | Yamasaki |
| H2013 H | 2/2002 | Boyd et al. |
| 6,387,918 B1 | 5/2002 | Yamanaka |
| 6,410,039 B1 | 6/2002 | Walker |
| 6,416,768 B1 | 7/2002 | Ravaux |
| 6,419,907 B1 | 7/2002 | Hocquaux |
| 6,432,415 B1 | 8/2002 | Osborne |
| 6,440,432 B1 | 8/2002 | Mukherjee |
| 6,440,437 B1 | 8/2002 | Krzysik |
| 6,461,622 B2 | 10/2002 | Liu |
| 6,468,549 B1 | 10/2002 | Dupuis |
| 6,492,326 B1 | 12/2002 | Robinson |
| 6,524,598 B2 | 2/2003 | Sunkel |
| 6,585,984 B1 | 7/2003 | Scott |
| 6,632,444 B1 | 10/2003 | Zhou |
| 6,638,519 B1 | 10/2003 | Lorant |
| 6,682,750 B2 | 1/2004 | Loeffler |
| 6,696,049 B2 | 2/2004 | Vatter et al. |
| 6,706,259 B1 | 3/2004 | Gardner |
| 6,759,051 B2 | 7/2004 | Saint-leger |
| 6,831,107 B2 | 12/2004 | Dederen |
| 6,903,210 B2 | 6/2005 | Behrends |
| 6,906,106 B2 | 6/2005 | Chevalier |
| 6,932,976 B2 | 8/2005 | Brooks |
| 6,979,452 B2 | 12/2005 | Zhou |
| 6,986,895 B2 | 1/2006 | Suares |
| 7,018,660 B2 | 3/2006 | Murad |
| 7,176,191 B2 | 2/2007 | Dale |
| 7,179,771 B1 | 2/2007 | Charlton |
| 7,291,351 B2 | 11/2007 | Azik |
| 7,300,678 B2 | 11/2007 | Paufique |
| 7,332,152 B2 | 2/2008 | Sanzgiri |
| 7,378,083 B2 | 5/2008 | Stephens |
| 7,416,719 B2 | 8/2008 | Huerta |
| 7,455,849 B2 | 11/2008 | Utschig |
| 7,741,366 B2 | 6/2010 | Mackles |
| 7,799,356 B2 | 9/2010 | Raschke |
| 7,815,900 B1 | 10/2010 | Cannell et al. |
| 7,829,107 B2 | 11/2010 | Popp |
| 8,063,097 B2 | 11/2011 | Robinson |
| 8,106,184 B2 | 1/2012 | Sauve |
| 8,197,807 B2 | 6/2012 | Brenner |
| 8,293,279 B2 | 10/2012 | Schiffer |
| 8,293,784 B2 | 10/2012 | Rudolph |
| 8,329,758 B2 | 12/2012 | Ali |
| 8,343,902 B2 | 1/2013 | Walters |
| 8,383,086 B2 | 2/2013 | Brenner |
| 8,435,950 B2 | 5/2013 | Dal |
| 8,475,851 B2 | 7/2013 | Herrmann |
| 8,491,464 B2 | 7/2013 | Yokoi |
| 8,529,920 B2 | 9/2013 | Liu |
| 8,529,979 B2 | 9/2013 | Abril |
| 8,546,364 B2 | 10/2013 | Patel |
| 8,652,447 B2 | 2/2014 | Maesen |
| 8,828,410 B2 | 9/2014 | Sakuta |
| 8,883,215 B2 | 11/2014 | Beck |
| 8,895,034 B2 | 11/2014 | Bennett |
| 8,895,513 B2 | 11/2014 | Trudsoe |
| 8,911,774 B2 | 12/2014 | Giampapa |
| 8,933,217 B2 | 1/2015 | Rinsch |
| 8,968,755 B2 | 3/2015 | Schlessinger |
| 8,999,923 B2 | 4/2015 | Cao et al. |
| 9,034,833 B1 | 5/2015 | Chiou et al. |
| 9,068,148 B2 | 6/2015 | Tamareselvy |
| 9,084,734 B2 | 7/2015 | Collier |
| 9,186,304 B2 | 11/2015 | Claas |
| 9,271,912 B2 | 3/2016 | Fernandez Prieto |
| 9,283,163 B2 | 3/2016 | Santhanam |
| 9,339,447 B2 | 5/2016 | Souzy |
| 9,364,414 B2 | 6/2016 | Domloge |
| 9,364,690 B2 | 6/2016 | Lorant |
| 9,381,144 B1 | 7/2016 | Hilt |
| 9,446,265 B2 | 9/2016 | Jansen et al. |
| 9,468,597 B1 | 10/2016 | Perry |
| 9,474,699 B2 | 10/2016 | Sun |
| 9,486,394 B2 | 11/2016 | Abram |
| 9,526,690 B2 | 12/2016 | Da Costa Pereira |
| 9,655,934 B2 | 5/2017 | Schiemann |
| 9,775,789 B2 | 10/2017 | Simmons |
| 9,795,544 B2 | 10/2017 | Lorant |
| 9,820,482 B2 | 11/2017 | Bingham |
| 9,833,398 B2 | 12/2017 | Hakozaki |
| 9,834,635 B2 | 12/2017 | Klug |
| 9,867,774 B1 | 1/2018 | Hakim |
| 9,895,300 B2 | 2/2018 | Schroeder |
| 9,949,902 B2 | 4/2018 | Mundschau |
| 10,124,030 B2 | 11/2018 | Goldsberry |
| 10,130,578 B2 | 11/2018 | Brillouet |
| 10,363,209 B2 | 7/2019 | Wu |
| 10,398,640 B2 | 9/2019 | Widgerow |
| 10,413,485 B2 | 9/2019 | Huang |
| 10,441,822 B2 | 10/2019 | Buckley |
| 10,449,126 B2 | 10/2019 | L'alloret |
| 10,660,838 B2 | 5/2020 | Hakozaki |
| 10,959,933 B1 | 3/2021 | Zhang et al. |
| 2001/0009671 A1 | 7/2001 | Helbiche |
| 2001/0024655 A1 | 9/2001 | Schneider |
| 2002/0022040 A1 | 2/2002 | Robinson et al. |
| 2002/0022052 A1 | 2/2002 | Dransfield |
| 2002/0042438 A1 | 4/2002 | Pelletier |
| 2002/0058704 A1 | 5/2002 | Malik |
| 2002/0168423 A1 | 11/2002 | Wurzburger |
| 2002/0193264 A1 | 12/2002 | Cannell et al. |
| 2003/0032617 A1 | 2/2003 | Harel et al. |
| 2003/0049212 A1 | 3/2003 | Robinson et al. |
| 2003/0091603 A1 | 5/2003 | Ohmori |
| 2003/0118620 A1 | 6/2003 | Zhang |
| 2003/0147968 A1 | 8/2003 | Farber |
| 2003/0158363 A1 | 8/2003 | Nakanishi |
| 2003/0165552 A1 | 9/2003 | Fox |
| 2003/0223982 A1 | 12/2003 | Schlotmann |
| 2004/0013784 A1 | 1/2004 | Costa |
| 2004/0028634 A1 | 2/2004 | Tanaka |
| 2004/0081672 A1 | 4/2004 | Gupta |
| 2004/0092482 A1 | 5/2004 | Gupta |
| 2004/0175347 A1 | 9/2004 | Bissett |
| 2004/0265268 A1 | 12/2004 | Jain |
| 2005/0008601 A1 | 1/2005 | Ariotto |
| 2005/0037036 A1 | 2/2005 | Nielsen |
| 2005/0100519 A1 | 5/2005 | Guth |
| 2005/0106194 A1 | 5/2005 | Schiltz |
| 2005/0170013 A1 | 8/2005 | Douglas |
| 2005/0176677 A1 | 8/2005 | Dal Farra et al. |
| 2005/0227327 A1 | 10/2005 | Brenner |
| 2005/0244348 A1 | 11/2005 | Lindemann |
| 2005/0267023 A1 | 12/2005 | Sinclair et al. |
| 2006/0018861 A1 | 1/2006 | Chen |
| 2006/0034875 A1 | 2/2006 | Nakanishi |
| 2006/0040851 A1 | 2/2006 | Ghosh |
| 2006/0127426 A1 | 6/2006 | Ross |
| 2006/0147508 A1 | 7/2006 | Gupta |
| 2006/0161121 A1 | 7/2006 | Klaveness |
| 2006/0165741 A1 | 7/2006 | Coffindaffer |
| 2006/0210499 A1 | 9/2006 | Hoeffkes |
| 2006/0229265 A1 | 10/2006 | Milburn et al. |
| 2006/0275237 A1 | 12/2006 | Bissett et al. |
| 2007/0027095 A1 | 2/2007 | Brenner |
| 2007/0196344 A1 | 8/2007 | Osborne et al. |
| 2007/0231288 A1 | 10/2007 | Arnaud et al. |
| 2007/0232508 A1 | 10/2007 | Oshimura |
| 2007/0232687 A1 | 10/2007 | Kato |
| 2008/0025932 A1 | 1/2008 | Bissett et al. |
| 2008/0057138 A1 | 3/2008 | Telford |

(56) References Cited

U.S. PATENT DOCUMENTS

| | | |
|---|---|---|
| 2008/0181956 A1 | 7/2008 | Ha |
| 2008/0206169 A1 | 8/2008 | Millikin |
| 2008/0206373 A1 | 8/2008 | Millikin |
| 2008/0247960 A1 | 10/2008 | Yuan |
| 2008/0287533 A1 | 11/2008 | Gupta |
| 2008/0312169 A1 | 12/2008 | Johnson et al. |
| 2008/0312181 A1 | 12/2008 | Harel et al. |
| 2008/0317795 A1 | 12/2008 | Traynor |
| 2009/0068219 A1 | 3/2009 | Elie |
| 2009/0196942 A1 | 8/2009 | Goyarts et al. |
| 2009/0197819 A1 | 8/2009 | Johnson et al. |
| 2009/0214628 A1 | 8/2009 | De Rijk |
| 2009/0215723 A1 | 8/2009 | Le |
| 2009/0232750 A1 | 9/2009 | St. Cyr |
| 2009/0317354 A1 | 12/2009 | Nishimura |
| 2010/0015072 A1 | 1/2010 | Polla et al. |
| 2010/0040608 A1 | 2/2010 | Wahren-Herlenius et al. |
| 2010/0092408 A1 | 4/2010 | Breyfogle et al. |
| 2010/0092412 A1 | 4/2010 | Gohier |
| 2010/0105638 A1 | 4/2010 | Den-braven |
| 2010/0183531 A1 | 7/2010 | Johncock |
| 2010/0189669 A1 | 7/2010 | Hakozaki |
| 2010/0203175 A1 | 8/2010 | Abdul-malak |
| 2010/0204323 A1 | 8/2010 | Theiler |
| 2010/0215726 A1 | 8/2010 | Roth |
| 2010/0239510 A1 | 9/2010 | Ha |
| 2010/0254919 A1 | 10/2010 | Bommarito |
| 2010/0272667 A1 | 10/2010 | Kyte, III et al. |
| 2010/0291190 A1 | 11/2010 | Giampapa |
| 2011/0097286 A1 | 4/2011 | Swanson |
| 2011/0101021 A1 | 5/2011 | Greer et al. |
| 2011/0117219 A1 | 5/2011 | Springer |
| 2011/0123467 A1 | 5/2011 | Roth |
| 2011/0152384 A1 | 6/2011 | Gunn |
| 2011/0158920 A1 | 6/2011 | Morley |
| 2011/0172160 A1 | 7/2011 | Cao |
| 2011/0229427 A1 | 9/2011 | Klug |
| 2011/0262025 A1 | 10/2011 | Jarrold et al. |
| 2011/0262560 A1 | 10/2011 | Dabe et al. |
| 2012/0003168 A1 | 1/2012 | Lyga et al. |
| 2012/0022013 A1 | 1/2012 | Sinclair et al. |
| 2012/0039967 A1 | 2/2012 | Lou |
| 2012/0093896 A1 | 4/2012 | Mongiat |
| 2012/0121534 A1 | 5/2012 | Thorel et al. |
| 2012/0128683 A1 | 5/2012 | Shantha |
| 2012/0148515 A1 | 6/2012 | Hakozaki et al. |
| 2012/0156146 A1 | 6/2012 | Hakozaki et al. |
| 2012/0172584 A1 | 7/2012 | Sauve et al. |
| 2012/0189684 A1 | 7/2012 | Buckley |
| 2012/0197016 A1 | 8/2012 | Laughlin, II et al. |
| 2012/0225050 A1 | 9/2012 | Knight et al. |
| 2013/0022557 A1 | 1/2013 | Swanson |
| 2013/0125317 A1 | 5/2013 | Rudolph |
| 2013/0164234 A1 | 6/2013 | Gruber |
| 2013/0164265 A1 | 6/2013 | Flavin |
| 2013/0189211 A1 | 7/2013 | Marini |
| 2013/0295024 A1 | 11/2013 | Hammer |
| 2013/0319449 A1 | 12/2013 | Xavier et al. |
| 2014/0020701 A1 | 1/2014 | Galderisi |
| 2014/0065099 A1 | 3/2014 | Alvarez et al. |
| 2014/0090660 A1 | 4/2014 | Xavier et al. |
| 2014/0127332 A1 | 5/2014 | Bitler |
| 2014/0158148 A1 | 6/2014 | Mette |
| 2014/0170195 A1 | 6/2014 | Fassih et al. |
| 2014/0190507 A9 | 7/2014 | Xavier et al. |
| 2014/0328774 A1 | 11/2014 | Rout et al. |
| 2014/0328775 A1 | 11/2014 | Laughlin, II et al. |
| 2014/0369943 A1 | 12/2014 | Pilz |
| 2015/0065476 A1 | 3/2015 | Aistrup |
| 2015/0118169 A1 | 4/2015 | Hakozaki et al. |
| 2015/0164941 A1 | 6/2015 | Munisekhar |
| 2015/0196464 A1 | 7/2015 | Jansen et al. |
| 2015/0209261 A1 | 7/2015 | Ross |
| 2015/0209272 A1 | 7/2015 | Weisman |
| 2015/0272860 A1 | 10/2015 | Mette |
| 2015/0272865 A1 | 10/2015 | Mette |
| 2015/0359723 A1 | 12/2015 | Kim |
| 2016/0074643 A1 | 3/2016 | Mcildowie et al. |
| 2016/0077080 A1 | 3/2016 | Laughlin, II et al. |
| 2016/0089324 A1 | 3/2016 | Nijakowski |
| 2016/0095806 A1 | 4/2016 | Farber |
| 2016/0102179 A1 | 4/2016 | Wagner |
| 2016/0128944 A1 | 5/2016 | Chawrai |
| 2016/0151270 A1 | 6/2016 | Brooks |
| 2016/0199404 A1 | 7/2016 | Blotsky |
| 2016/0235646 A1 | 8/2016 | Shah et al. |
| 2016/0250134 A1 | 9/2016 | Castle |
| 2016/0250241 A1 | 9/2016 | Deren-Lewis et al. |
| 2016/0317418 A1 | 11/2016 | Hakazaki et al. |
| 2016/0317419 A1 | 11/2016 | Hakazaki et al. |
| 2016/0317420 A1 | 11/2016 | Hakazaki et al. |
| 2016/0374908 A1 | 12/2016 | Hakozaki et al. |
| 2016/0374918 A1 | 12/2016 | Dihora et al. |
| 2016/0374919 A1 | 12/2016 | Hakozaki et al. |
| 2017/0079408 A1 | 3/2017 | Lee |
| 2017/0121746 A1 | 5/2017 | Velasquez et al. |
| 2017/0165160 A1 | 6/2017 | Schulze Zur Wiesche |
| 2017/0172972 A1 | 6/2017 | Buge |
| 2017/0196795 A1 | 7/2017 | Hakozaki |
| 2017/0227011 A1 | 8/2017 | Zhou et al. |
| 2017/0266099 A1 | 9/2017 | Kroon |
| 2017/0333321 A1 | 11/2017 | Carnali |
| 2017/0360674 A1 | 12/2017 | Schulze Zur Wiesche |
| 2018/0015013 A1 | 1/2018 | Prendergast |
| 2018/0042840 A1 | 2/2018 | Almiñana Domènech |
| 2018/0104175 A1 | 4/2018 | Liu |
| 2018/0140518 A1 | 5/2018 | Deckner |
| 2018/0177703 A1 | 6/2018 | Perricone |
| 2018/0185283 A1 | 7/2018 | Buge |
| 2018/0271760 A1 | 9/2018 | Baca |
| 2018/0271881 A1 | 9/2018 | Buge |
| 2018/0280297 A1 | 10/2018 | Buge |
| 2018/0280298 A1 | 10/2018 | Buge |
| 2018/0311137 A1 | 11/2018 | Mckiernan |
| 2018/0344624 A1 | 12/2018 | Athwal |
| 2018/0369110 A1 | 12/2018 | Hakozaki |
| 2019/0021961 A1 | 1/2019 | Abels |
| 2019/0076811 A1 | 3/2019 | Lei |
| 2019/0125654 A1 | 5/2019 | Goldsberry |
| 2019/0240141 A1 | 8/2019 | Boland |
| 2019/0328631 A1 | 10/2019 | Lou |
| 2019/0380945 A1 | 12/2019 | Hakozaki |
| 2020/0002377 A1 | 1/2020 | Van Den Nest |
| 2020/0253851 A1 | 8/2020 | Hakozaki |
| 2021/0369588 A1 | 12/2021 | Zhang et al. |

FOREIGN PATENT DOCUMENTS

| | | |
|---|---|---|
| BR | 102013005446 A2 | 6/2015 |
| CA | 2517765 C | 7/2009 |
| CA | 2217032 C | 12/2009 |
| CH | 711092 A2 | 11/2016 |
| CN | 101182299 A | 5/2008 |
| CN | 100418507 C | 9/2008 |
| CN | 100457074 C | 2/2009 |
| CN | 101048375 B | 12/2012 |
| CN | 103070781 A | 5/2013 |
| CN | 103211717 A | 7/2013 |
| CN | 102670469 B | 10/2013 |
| CN | 103565721 A | 2/2014 |
| CN | 102871863 B | 4/2014 |
| CN | 102716511 B | 5/2014 |
| CN | 104274340 A | 1/2015 |
| CN | 104688617 A | 6/2015 |
| CN | 104688654 A | 6/2015 |
| CN | 104784084 A | 7/2015 |
| CN | 104812363 A | 7/2015 |
| CN | 104873436 A | 9/2015 |
| CN | 104983630 A | 10/2015 |
| CN | 105168677 A | 12/2015 |
| CN | 104168883 B | 5/2016 |
| CN | 105769747 A | 7/2016 |
| CN | 103987372 B | 8/2016 |
| CN | 104095770 B | 8/2016 |

(56) References Cited

FOREIGN PATENT DOCUMENTS

| | | |
|---|---|---|
| CN | 105997548 A | 10/2016 |
| CN | 106214607 A | 12/2016 |
| CN | 106456476 A | 2/2017 |
| CN | 106729669 A | 5/2017 |
| CN | 106821849 A | 6/2017 |
| CN | 107137299 A | 9/2017 |
| CN | 107320355 A | 11/2017 |
| CN | 107427429 A | 12/2017 |
| CN | 108078889 A | 5/2018 |
| CN | 105640870 B | 12/2018 |
| CN | 108938445 A | 12/2018 |
| CN | 109010216 A | 12/2018 |
| CN | 109106806 A | 1/2019 |
| DE | 1949740 A1 | 7/1970 |
| DE | 2423637 A1 | 11/1975 |
| DE | 3029263 A1 | 3/1981 |
| DE | 10063658 A1 | 7/2002 |
| DE | 10063660 A1 | 7/2002 |
| DE | 10139582 A1 | 2/2003 |
| DE | 20220609 U1 | 12/2003 |
| DE | 60104036 T2 | 8/2004 |
| DE | 69828095 T2 | 1/2005 |
| DE | 102004008440 A1 | 9/2005 |
| DE | 102004035737 A1 | 3/2006 |
| DE | 60030917 T2 | 11/2006 |
| DE | 60032597 T2 | 2/2007 |
| DE | 19712980 B4 | 10/2008 |
| DE | 102007036499 A1 | 2/2009 |
| DE | 102007037432 A1 | 2/2009 |
| DE | 102008010921 A1 | 9/2009 |
| DE | 102010026465 A1 | 5/2011 |
| DE | 102010027180 A1 | 5/2011 |
| DE | 102011084904 A1 | 6/2012 |
| DE | 102011087883 A1 | 8/2012 |
| DE | 102011089357 A1 | 8/2012 |
| DE | 102011089612 A1 | 6/2013 |
| DE | 102013225182 A1 | 4/2014 |
| EP | 0315541 A1 | 5/1989 |
| EP | 0350275 A3 | 6/1991 |
| EP | 0826366 A3 | 4/1998 |
| EP | 0995427 A3 | 5/2000 |
| EP | 1417954 A1 | 5/2004 |
| EP | 1459736 A1 | 9/2004 |
| EP | 1618867 A1 | 1/2006 |
| EP | 1815843 A2 | 8/2007 |
| EP | 1949887 A2 | 7/2008 |
| EP | 1779845 B1 | 10/2010 |
| EP | 1997537 A3 | 2/2012 |
| EP | 2020227 B1 | 8/2012 |
| EP | 2548549 A1 | 1/2013 |
| EP | 2033622 B1 | 3/2013 |
| EP | 1276513 B1 | 11/2013 |
| EP | 2057980 B1 | 4/2014 |
| EP | 1435771 B1 | 7/2015 |
| EP | 1609462 B1 | 7/2015 |
| EP | 3040065 A1 | 7/2016 |
| EP | 2793828 B1 | 8/2016 |
| EP | 3050900 A1 | 8/2016 |
| EP | 1776161 B1 | 10/2016 |
| EP | 1852102 B1 | 10/2016 |
| EP | 1904020 B1 | 10/2016 |
| EP | 2308456 B1 | 10/2016 |
| EP | 1786893 B2 | 11/2016 |
| EP | 1672037 B1 | 12/2016 |
| EP | 1813255 B1 | 11/2017 |
| EP | 1475080 B1 | 4/2018 |
| EP | 2263788 B1 | 7/2018 |
| EP | 3220883 B1 | 7/2018 |
| EP | 2696841 B1 | 10/2018 |
| EP | 3122325 B1 | 10/2018 |
| EP | 2677999 B1 | 12/2018 |
| ES | 2236040 T3 | 7/2005 |
| ES | 2222818 B1 | 3/2007 |
| ES | 2542529 T3 | 8/2015 |
| FR | 1464035 A | 7/1966 |
| FR | 2366841 B1 | 2/1980 |
| FR | 2555443 A1 | 5/1985 |
| FR | 2586693 A1 | 3/1987 |
| FR | 2832062 B1 | 2/2004 |
| FR | 2845596 A1 | 4/2004 |
| FR | 2845284 B1 | 12/2004 |
| FR | 2883170 A1 | 9/2006 |
| FR | 2883171 B1 | 5/2007 |
| FR | 2938188 A1 | 5/2010 |
| FR | 2975295 A1 | 11/2012 |
| FR | 2986429 A1 | 8/2013 |
| FR | 2989891 A1 | 11/2013 |
| GB | 2050829 B | 10/1983 |
| GB | 2270259 A | 3/1994 |
| GB | 2472379 A | 2/2011 |
| JP | H0141602 B2 | 9/1989 |
| JP | H0237206 B2 | 8/1990 |
| JP | H0892061 A | 4/1996 |
| JP | H11137212 A | 5/1999 |
| JP | 2954640 B2 | 9/1999 |
| JP | H11240827 A | 9/1999 |
| JP | 2000072616 A | 3/2000 |
| JP | 2000109421 A | 4/2000 |
| JP | 2000119155 A | 4/2000 |
| JP | 2000212061 A | 8/2000 |
| JP | 2001064150 A * | 3/2001 |
| JP | 2001089316 A | 4/2001 |
| JP | 2001107078 A | 4/2001 |
| JP | 2001261570 A | 9/2001 |
| JP | 2002080335 A | 3/2002 |
| JP | 2002145723 A | 5/2002 |
| JP | 2003095842 A | 4/2003 |
| JP | 2003261437 A | 9/2003 |
| JP | 3519269 B2 | 4/2004 |
| JP | 2004123871 A | 4/2004 |
| JP | 2004137176 A | 5/2004 |
| JP | 2004161655 A | 6/2004 |
| JP | 2004210699 A | 7/2004 |
| JP | 2004210700 A | 7/2004 |
| JP | 2004217616 A | 8/2004 |
| JP | 3615759 B2 | 11/2004 |
| JP | 3643038 B2 | 2/2005 |
| JP | 2005035910 A | 2/2005 |
| JP | 2005041861 A | 2/2005 |
| JP | 2005139139 A | 6/2005 |
| JP | 2005162741 A | 6/2005 |
| JP | 2005232092 A | 9/2005 |
| JP | 2005281133 A | 10/2005 |
| JP | 3739100 B2 | 11/2005 |
| JP | 2005306751 A | 11/2005 |
| JP | 2005320260 A | 11/2005 |
| JP | 3747141 B2 | 12/2005 |
| JP | 2006028133 A | 2/2006 |
| JP | 2006143777 A | 6/2006 |
| JP | 3863675 B2 | 10/2006 |
| JP | 2007106697 A | 4/2007 |
| JP | 2007145716 A | 6/2007 |
| JP | 2007297559 A | 11/2007 |
| JP | 4072296 B2 | 1/2008 |
| JP | 2008143838 A | 6/2008 |
| JP | 2008231010 A | 10/2008 |
| JP | 2009024075 A | 2/2009 |
| JP | 4399332 B2 | 10/2009 |
| JP | 2009269919 A | 11/2009 |
| JP | 4589050 B2 | 9/2010 |
| JP | 2010202595 A | 9/2010 |
| JP | 4759912 B2 | 6/2011 |
| JP | 2011213676 A | 10/2011 |
| JP | 2011236176 A | 11/2011 |
| JP | 4931356 B2 | 2/2012 |
| JP | 2012097030 A | 5/2012 |
| JP | 5203623 B2 | 2/2013 |
| JP | 2013053147 A | 3/2013 |
| JP | 2013103892 A | 5/2013 |
| JP | 2013116884 A | 6/2013 |
| JP | 2013121955 A | 6/2013 |
| JP | 2013173730 A | 9/2013 |
| JP | 2013194030 A | 9/2013 |
| JP | 5427422 B2 | 12/2013 |

(56) References Cited

FOREIGN PATENT DOCUMENTS

| | | |
|---|---|---|
| JP | 2014001155 A | 1/2014 |
| JP | 2014051670 A | 3/2014 |
| JP | 2014062077 A | 4/2014 |
| JP | 2014080374 A | 5/2014 |
| JP | 2015500269 A | 1/2015 |
| JP | 2015147752 A | 8/2015 |
| JP | 2015178485 A | 10/2015 |
| JP | 5857104 B2 | 12/2015 |
| JP | 2016003199 A | 1/2016 |
| JP | 2016027037 A | 2/2016 |
| JP | 2016504377 A | 2/2016 |
| JP | 2016044171 A | 4/2016 |
| JP | 2016069306 A | 5/2016 |
| JP | 2016077836 A | 5/2016 |
| JP | 2016098199 A | 5/2016 |
| JP | 6005863 B2 | 9/2016 |
| JP | 2016183152 A | 10/2016 |
| JP | 2016532654 A | 10/2016 |
| JP | 6017953 B2 | 11/2016 |
| JP | 2016536305 A | 11/2016 |
| JP | 2017501225 A | 1/2017 |
| JP | 6183849 B2 | 8/2017 |
| JP | 6184825 B2 | 8/2017 |
| JP | 2017529368 A | 10/2017 |
| JP | 2017210408 A | 11/2017 |
| JP | 6362243 B2 | 7/2018 |
| JP | 2018168102 A | 11/2018 |
| KR | 20000024485 A * | 5/2000 |
| KR | 20050006622 A | 1/2005 |
| KR | 20070014412 A | 2/2007 |
| KR | 20080082802 A | 9/2008 |
| KR | 20110007751 A | 1/2011 |
| KR | 20120087600 A | 8/2012 |
| KR | 20130088224 A | 8/2013 |
| KR | 20140001686 A | 1/2014 |
| KR | 20140055689 A | 5/2014 |
| KR | 101405615 B1 | 6/2014 |
| KR | 20140093349 A | 7/2014 |
| KR | 20140132243 A | 11/2014 |
| KR | 20150066811 A | 6/2015 |
| KR | 20160002093 A | 1/2016 |
| KR | 20160096548 A | 8/2016 |
| KR | 20160101371 A | 8/2016 |
| KR | 20160108971 A | 9/2016 |
| KR | 20160109869 A | 9/2016 |
| KR | 20180008071 A | 1/2018 |
| KR | 20180020664 A | 2/2018 |
| KR | 20180036232 A | 4/2018 |
| KR | 20180060701 A | 6/2018 |
| KR | 20190001136 A | 1/2019 |
| RU | 2400213 C2 | 9/2010 |
| TW | 201244748 A | 11/2012 |
| WO | 8806888 A1 | 9/1988 |
| WO | 9217159 A3 | 1/1993 |
| WO | 9307856 A1 | 4/1993 |
| WO | 9416710 A1 | 8/1994 |
| WO | 9524179 A1 | 9/1995 |
| WO | 9603970 A1 | 2/1996 |
| WO | 9720540 A1 | 6/1997 |
| WO | 9720542 A1 | 6/1997 |
| WO | 9823256 A1 | 6/1998 |
| WO | 9856343 A1 | 12/1998 |
| WO | 9920229 A1 | 4/1999 |
| WO | 9947141 A1 | 9/1999 |
| WO | 9943296 A3 | 11/1999 |
| WO | 9960995 A1 | 12/1999 |
| WO | 0024921 A1 | 5/2000 |
| WO | 0071093 A1 | 11/2000 |
| WO | 0170187 A1 | 9/2001 |
| WO | 0170188 A1 | 9/2001 |
| WO | 0181635 A1 | 11/2001 |
| WO | 0207685 A2 | 1/2002 |
| WO | 0207700 A2 | 1/2002 |
| WO | 0219984 A3 | 8/2002 |
| WO | 03022234 A1 | 3/2003 |
| WO | 2004024115 A1 | 3/2004 |
| WO | 2005004829 A1 | 1/2005 |
| WO | 2005004833 A1 | 1/2005 |
| WO | 2004100862 A3 | 2/2005 |
| WO | 2005034969 A1 | 4/2005 |
| WO | 2005044214 A1 | 5/2005 |
| WO | 2005049782 A1 | 6/2005 |
| WO | 2006040048 A1 | 4/2006 |
| WO | 2006081071 A1 | 8/2006 |
| WO | 2006127987 A2 | 11/2006 |
| WO | 2007002831 A2 | 1/2007 |
| WO | 2007101493 A1 | 9/2007 |
| WO | 200800534 A1 | 1/2008 |
| WO | 2008003779 A1 | 1/2008 |
| WO | 2008016298 A1 | 2/2008 |
| WO | 2007067735 A3 | 3/2008 |
| WO | 2009099419 A3 | 5/2010 |
| WO | 2009150408 A3 | 5/2010 |
| WO | 2010051852 A1 | 5/2010 |
| WO | 2010058272 A3 | 7/2010 |
| WO | 2011030123 A2 | 3/2011 |
| WO | 2011033858 A1 | 3/2011 |
| WO | 2011004175 A3 | 4/2011 |
| WO | 2011052224 A1 | 5/2011 |
| WO | 2011074143 A1 | 6/2011 |
| WO | 2012172199 A1 | 12/2012 |
| WO | 2013010032 A1 | 1/2013 |
| WO | 2013088371 A2 | 6/2013 |
| WO | 2011139492 A3 | 7/2013 |
| WO | 2013124820 A1 | 8/2013 |
| WO | 2011038022 A3 | 9/2013 |
| WO | 2013143776 A2 | 10/2013 |
| WO | 2014090513 A1 | 6/2014 |
| WO | 2014131514 A1 | 9/2014 |
| WO | 2014132060 A1 | 9/2014 |
| WO | 2014190128 A1 | 11/2014 |
| WO | 2015007567 A1 | 1/2015 |
| WO | 2015030702 A2 | 3/2015 |
| WO | 2015061512 A1 | 4/2015 |
| WO | 2015117757 A1 | 8/2015 |
| WO | 2015186114 A1 | 12/2015 |
| WO | 2016006821 A1 | 1/2016 |
| WO | 2016034519 A1 | 3/2016 |
| WO | 2015174772 A9 | 6/2016 |
| WO | 2016097965 A1 | 6/2016 |
| WO | 2016100634 A2 | 6/2016 |
| WO | 2016142551 A1 | 9/2016 |
| WO | 2016171464 A1 | 10/2016 |
| WO | 2016188691 A1 | 12/2016 |
| WO | 2017093788 A1 | 6/2017 |
| WO | 2017123512 A1 | 7/2017 |
| WO | 2017174756 A1 | 10/2017 |
| WO | 2017191382 A1 | 11/2017 |
| WO | 2017194268 A1 | 11/2017 |
| WO | 2017194292 A1 | 11/2017 |
| WO | 2017200979 A1 | 11/2017 |
| WO | 2018062922 A1 | 4/2018 |
| WO | 2018071640 A1 | 4/2018 |
| WO | 2018112586 A1 | 6/2018 |
| WO | 2018134714 A1 | 7/2018 |
| WO | 2018160509 A1 | 9/2018 |
| WO | 2018189194 A1 | 10/2018 |
| WO | 2018191296 A1 | 10/2018 |
| WO | 2018206962 A1 | 11/2018 |
| WO | 2019245011 A1 | 12/2019 |

OTHER PUBLICATIONS

Gillbro, et al., The use of gene arrays and corresponding connectivity mapping (Cmap) to identify novel anti-ageing ingredients, International Journal of Cosmetic Science, 2015, 37 (Suppl. 1), 9-14.

International Search Report and Written Opinion of the International Searching Authority, PCT/US2018/038903, dated Aug. 31, 2018, 16 pages.

International Search Report and Written Opinion of the International Searching Authority, PCT/US2019/037430, dated Sep. 30, 2019, 12 pages.

(56) References Cited

OTHER PUBLICATIONS

Khalifah et al., Kinetics of Nonenzymatic Glycation of Ribonuclease A Leading to Advanced Glycation End Products. Paradoxical Inhibition by Ribose Leads to Facile Isolation of Protein Intermediate for Rapid Post-Amadori Studies, Biochemistry, vol. 35, No. 15, Apr. 16, 1996, pp. 4645-4654.
Stillman A.E., Jaundice, Clinical Methods: The History, Physical and Laboratory Examinations, 3rd edition, Chapter 87, 1990. Available from: https://www.ncbi.nlm.nih.gov/books/NBK413/.
Trojahn et al., Characterizing Facial Skin Ageing in Humans : Disentangling Extrinsic from Intrinsic Biological Phenomena, BioMed Research International, vol. 2015, Article ID 318586, 9 pages, http://dx.doi.org/10.1155/2015/318586, Jan. 14, 2015.
www.gnpd.com Record ID: 2347755, Dark Circle Correcting Eye Swirl, Apr. 2014.
www.gnpd.com Record ID: 3708793, Anti-Wrinkle Face Cream, Neogen Agecure, Mar. 2016.
U.S. Appl. No. 62/155,672, filed May 1, 2015, Tomohiro NMN Hakozaki et al.
"Breakout Star Oil-Free Acne Moisturizer", ID#7460333, Tula Life, USA, Mintel GNPD [online], Mar. 2020, Retrieved from Internet: URL:https://portal.mintel.com.
All Office Actions, U.S. Appl. No. 17/215,988.
All Office Actions, U.S. Appl. No. 17/335,718.
Unpublished U.S. Appl. No. 17/215,988, filed Mar. 29, 2021, to first inventor Lu (NMN) Zhang.
Unpublished U.S. Appl. No. 17/335,718, filed Jun. 1, 2021, to first inventor Lu Zhang.
All Office Actions, U.S. Appl. No. 16/460,308.
All Office Actions, U.S. Appl. No. 16/891,491.
Draelos et al., "Niacinamide-containing facial moisturizer improves skin barrier and benefits subjects with rosacea", Cutis, vol. 76, Aug. 2005, pp. 135-141.
Seppic, "Sepimax (TM) Zen", Datasheet, 2015. 4 Pages.
Soma et al., "Moisturizing effects of topical nicotinamide on atopic dry skin", International Journal of Dermatology, vol. 44, No. 3, Mar. 2005, pp. 197-202.
Superdrug B., "Confident Night Serum", https://www.skincarisma.com/products/b/confident-night-serum/ingredient_list#info-section, 14 pages.
www.gnpd.com Record ID: 3497875, Tria Age-Defying Skincare Nourishing Eye Renewal Cream, Nov. 2015, 05 pages.
All Office Actions; U.S. Appl. No. 17/335,674, filed Jun. 1, 2021.
Amico et al.,"Effects of Adalimumab, Etanercept and Ustekinumab on the Expression of Psoriasin (S100A7) in Psoriatic Skin", Journal Of Dermatological Science, vol. 80, Issue 1, Oct. 2015, 7 pages.
Chen Jian, Principles of Food Chemistry, South China University of Technology Press, dated Feb. 28, 2015, pp. 145-146.
Mintel, Sym-Micro Essence, Retrieved from Internet: http://www.gnpd.com, May 2020, 9 pages.
A.B. Kimball et al., Reduction in the appearance of facial hyperpigmentation after use of moisturizers with a combination of topical niacinamide and N-acetyl glucosamine: results of a randomized, double-blind, vehicle-controlled trial, British Journal of Dermatology 2010, vol. 162, No. 2, pp. 435-441.
All Office Actions, U.S. Appl. No. 15/402,332.
Ebanks, et al., Mechanisms Regulating Skin Pigmentation: The Rise and Fall of Complexion Coloration, International Journal of Molecular Sciences, 2009, vol. 10, pp. 4066-4087.
Ekman, et al., Overexpression of Psoriasin (S100A7) Contributes to Dysregulated Differentiation in Psoriasis, Acta Derm Venereol, Apr. 6, 2017, 97(4); 441-448.
Ferraz, et al., Kinetic α-Deuterium Isotope Effects for Enzymatic and Nonenzymatic Hydrolysis of Nicotinamide-β-Riboside, Archives of Biochemistry and Biophysics, vol. 191, No. 2, December pp. 431-436, 1978, 6 pages.
Glaser, et al., The Antimicrobial Protein Psoriasin (S100A7) Is Upregulated in Atopic Dermatitis and after Experimental Skin Barrier Disruption, Journal of Investigative Dermatology (2009), 129(3), 641-649; published online Aug. 28, 2008.
Hakozaki et al., The effect of niacinamide on reducing cutaneous pigmentation and suppression of melanosome transfer, British Journal of Dermatology (2002) vol. 147, No. 1: 20-31.
International Search Report and Written Opinion of the International Searching Authority, PCT/US2016/029943, dated Jul. 1, 2016, 19 pages.
International Search Report and Written Opinion of the International Searching Authority, PCT/US2016/029945, dated Jun. 27, 2016, 15 pages.
International Search Report and Written Opinion of the International Searching Authority, PCT/US2016/029951, dated Aug. 23, 2016, 2019, 11 pages.
International Search Report and Written Opinion of the International Searching Authority, PCT/US2016/039924, dated Aug. 26, 2016, 11 pages.
International Search Report and Written Opinion of the International Searching Authority, PCT/US2016/039925, dated Aug. 25, 2016, 11 pages.
International Search Report and Written Opinion of the International Searching Authority, PCT/US2016/039926, dated Aug. 22, 2016, 11 pages.
International Search Report and Written Opinion of the International Searching Authority, PCT/US2017/012786, dated Mar. 20, 2017, 13 pages.
International Search Report and Written Opinion of the International Searching Authority, PCT/US2019/040223, dated Oct. 25, 2019, 13 pages.
Oppenheimer, NAD Hydrolysis: Chemical and Enzymatic Mechanisms, Molecular and Cellular Biochemistry 138: 245-251, 1994.
Sinthupoom et al., Nicotinic acid and derivatives as multifunctional pharmacophores for medical applications, European Food Research and Technology, vol. 240, No. 1, Oct. 29, 2014, pp. 1-17.
Wohlrab, et al., Niacinamide—Mechanisms of Action and its Topical Use in Dermatology, Skin Pharmacology and Physiology 2014;27:311-315.
Zackheim H.S., Treatment of Psoriasis With 6-Aminonicotinamide. Arch Dermatol. 1975;111(7):880-882. doi:10.1001/archderm.1975.01630190070007.

\* cited by examiner

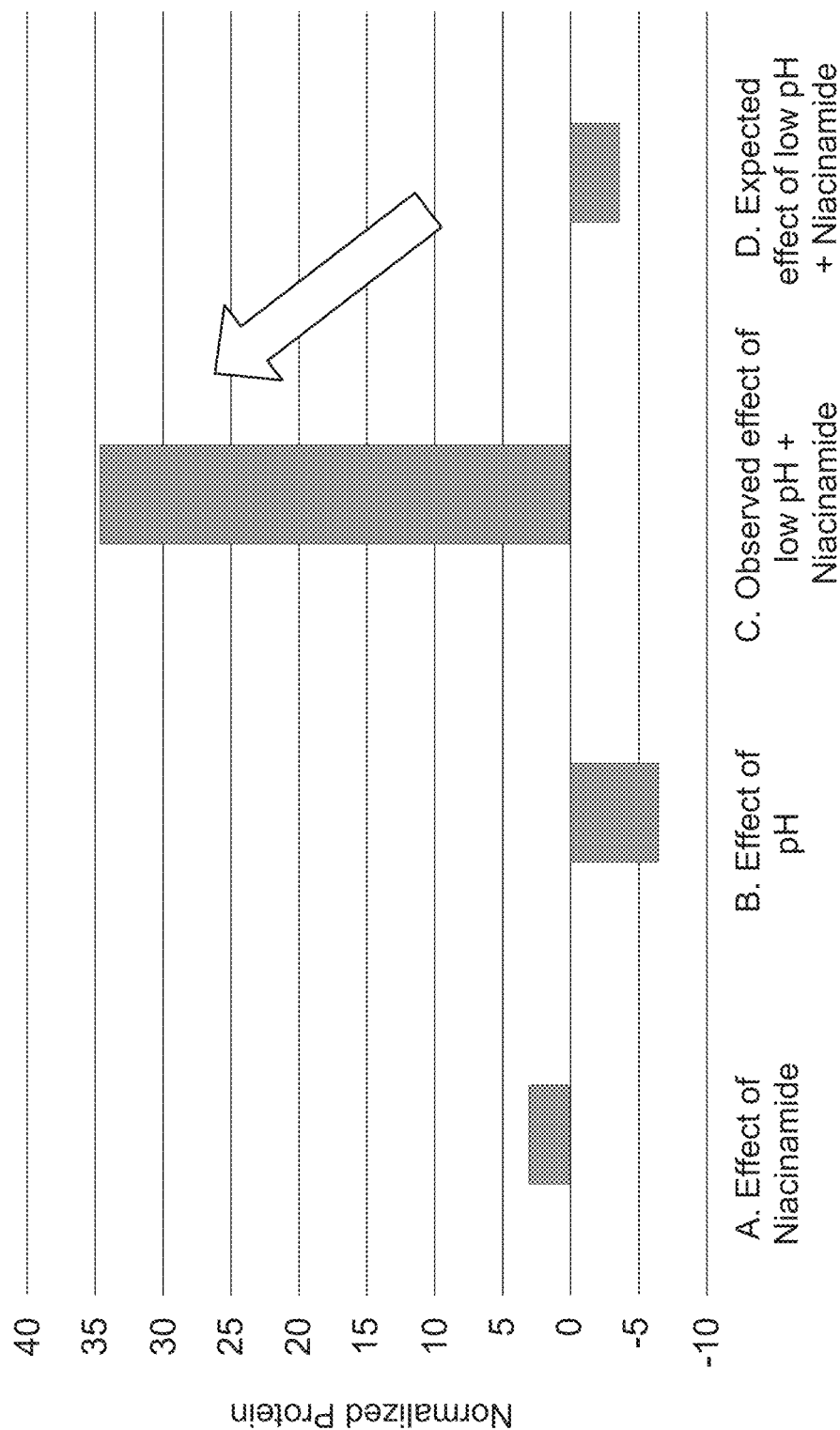

SEQUENCE LISTING

```
<160> NUMBER OF SEQ ID NOS: 2

<210> SEQ ID NO 1
<211> LENGTH: 2918
<212> TYPE: DNA
<213> ORGANISM: Homo sapiens

<400> SEQUENCE: 1
gtccaaacac acacatctca ctcatccttc tactcgtgac gcttcccagc tctggtaagt      60
ctcacctgcc tctttgcgtt ttctagaagt gcccagtgcc tggcctgcca tgctgcctgt     120
aggaagggaa agggctgtgg acaaagactc agaagcctgg gtctaggcca gctctgccat     180
tagctgggct gtgtgacctt cacttgaccc caaaagccca cgtctgtata accaggtggc     240
tgaaccagac ctgtccattg ctcctttggg atctcctgag gcaactcctg tggaaatgtc     300
cccagtggga cctgagcaca ggaccctccc tgtcctcttc ctccctggat tcatcctcct     360 gttgggtcc cggttgctaa atcccctccc cagctccagc tccacagagg gtggagggct     420
aggggtcccc tgtgaatgct ttggaggctc tccaaacccc caggcctggg accccgacac     480
agcatagccc tggccagatg gcttgcccct acctgggtaa ggtattgaga aaccaacgct     540
ccgtcactcc ctaccacaac ctgcaaattg tcagtcaccc tctgggcaca gggcttgccc     600
tctggccttg gcctcagatt caaaaaagct ctgggtggct cctcttagtc agttgccggc     660
atggagcttt ctcctgcatt gagaggtgtt gggggtttat tgtcagacac ccatatgcat     720
tagccaaggt ccttttcctgg ttctttggaa agtgtgggaa gtgagaactg cactgtccta     780
tttttcaggc ttggggtgca ggccagccca gactgactac tggctgaaag atctgctttg     840
```

```
ggaagtcaga cattttttatt taaacagtca aggcttggtg attcagaggg tgcagataat      900
tcccaagagc agacatgaag tgactcccac ctcactccca ccccgtccag cagcttaaga      960
accagagagt tatttctgtt ccttgtaaca gaggccattc ctgtttctcg ttcccaaggg     1020
aatacaagaa gggccccctg tgctcgggac aggactgtgt tcctgctaa cactcacgtc     1080 cacgctcaca tgtgcacctg agcctgcac acaccgtgtc atgcagggct tgcacttgag     1140
tcaaggtggg gcccacggtg tctggttcct gaagcagccg aggagggtca gacaccagat     1200
caccaaggcc attgtcctgc ccccatgact gtcaccccga ctgtgaagct ggaggagatg     1260
gatttggtgc tcttttaaga gtggggtctg ccatgtgctg gctgaggctg gggtgtccca     1320
gcttagttct tccatgtgtt gctggcgccc gactctccct gcttctccct ctctgaagca     1380
ctgtccacag ctggacttcc gccatccacc tgcatctcct cttggccctg ccaggatgg     1440 gccaggtctc agacttggtc ctaccctctc atttttgagc aacttatccc atcacattaa     1500
aaaaaaattg agttcgttct gctacacctt atccgtgttt ttactctgtc ctcagccctc     1560
cttccagcac tcccaaatag agaccctaac ttaaatgaag ggaaaaaaat gattgtcttt     1620
atttcctgaa ggcttttga aagcaaagat gagcaacact caagctgaga ggtccataat     1680
aggcatgatc gacatgtttc acaaatacac cagacgtgat gacaagattg agaagccaag     1740
cctgctgacg atgatgaagg agaacttccc caacttcctt agtgcctgtg tgagtcggtg     1800
tctagcttct caatgttgga ggatacattt tgctatgtgg ccttggacag atcaccctca     1860
ccctctgatt aaaaaatttc ccatttgcaa atagggcttt attacttgga tcatatgtga     1920
atctaaggat ggtaggcaaa aaagtatgaa aatgggaaag agttatacag atataaagga     1980
ggttattaga tggtcagcaa agtgtgcagc ttgagggcag tgcacagtcc cctcccagca     2040
ctcactgacc ctctctctgt gagactgaaa ctcacatgct caggtcctgt ttcccaaagg     2100
ccccacatca acatccctga gattactggg aaagcactag aagttccatt gttagtagaa     2160
atcaatagcc ctctttgcaa taaacaagac tcattagcaa atctgaaaaa aaactgtggg     2220
ctactaggta ccaaagggtc tagatgacca agagtaggat acccagaaga tgagtttggt     2280
ggaaaaggag aagaaggag aggaggccag agaaagaaga gaacaaaagc atgagggcca     2340
attttgaggc cctggggtag aactaaggta ggcagtgccc ttagaggctg ggacgggaaa     2400
gagtgaggct ggggcagggg actgctctcc ccaaggtcac ttaacagagc accttgggac     2460
aggacctgcc tcccatcctg aggtgtgaga caaaaagact ccctagagaa ctccagggat     2520
aacactcacg tcctcacccc aacttcaccc actcaccctg tgctctcagc ccgccacca     2580 tgcctgtgca gatctaggta cttgtctgta tctctgcctc ctcctctccc tcccagccca     2640
aaacttgttt gtgattgaat ttttctattt tgtatgtttt tctcttcaca ggacaaaaag     2700
ggcacaaatt acctcgccga tgtctttgag aaaaaggaca agaatgagga taagaagatt     2760
gatttttctg agttttctgtc cttgctggga gacatagcca cagactacca caagcagagc     2820
catggagcag cgccctgttc cggggggcagc cagtgaccca gccccaccaa tgggcctcca     2880 gagacccccag gaacaataaa atgtcttctc ccaccaga                            2918
```

<210> SEQ ID NO 2
<211> LENGTH: 101
<212> TYPE: PRT
<213> ORGANISM: Homo sapiens

<400> SEQUENCE: 2

Met Ser Asn Thr Gln Ala Glu Arg Ser Ile Ile Gly Met Ile Asp Met

-continued

```
1               5                   10                  15
Phe His Lys Tyr Thr Arg Arg Asp Asp Lys Ile Glu Lys Pro Ser Leu
            20                  25                  30

Leu Thr Met Met Lys Glu Asn Phe Pro Asn Phe Leu Ser Ala Cys Asp
            35              40                  45

Lys Lys Gly Thr Asn Tyr Leu Ala Asp Val Phe Glu Lys Lys Asp Lys
        50              55                  60

Asn Glu Asp Lys Lys Ile Asp Phe Ser Glu Phe Leu Ser Leu Leu Gly
65                  70              75                      80

Asp Ile Ala Thr Asp Tyr His Lys Gln Ser His Gly Ala Ala Pro Cys
                85                  90                  95

Ser Gly Gly Ser Gln
                100
```

METHOD OF TREATING A SKIN CONDITION

FIELD

The present disclosure is directed generally to a method of treating the symptoms of a skin barrier condition. More specifically, the present disclosure is directed to a method of treating the symptoms of psoriasis and/or atopic dermatitis with an effective amount of a vitamin $B_3$ compound in a low-pH composition.

BACKGROUND

Skin is the first line of defense against environmental insults that would otherwise damage sensitive underlying tissue and organs. For example, skin maintains a relatively water-impermeable barrier between an organism and its environment to prevent dehydration. Additionally, skin plays a key role in a person's physical appearance. Generally, most people desire to have healthy skin that looks healthy and maintains adequate barrier protection. However, a variety of intrinsic and extrinsic factors can lead to a decline in skin appearance and barrier function. For example, skin conditions such as psoriasis and atopic dermatitis (e.g., eczema) can result in itchy, red, and/or scaly patches of skin that impair the ability of skin to provide adequate barrier function.

Numerous agents, both natural and synthetic, are known for use in skin care compositions marketed to treat various skin conditions, especially those associated with psoriasis and atopic dermatitis. One example of a well-known skin care agent used in cosmetic skin agents is niacinamide U.S. Pat. No. 5,833,998 discloses the use of niacinamide for regulating the oily/shiny appearance on skin, and U.S. Pat. No. 5,968,528 discloses the use of niacinamide for regulating the signs of skin aging.

In some instances, the combination of niacinamide and other skin agents has been disclosed. For example, US 2012/0121534 and U.S. Pat. No. 5,053,230 disclose compositions for promoting the growth of skin cells to improve the appearance of wrinkled skin. The compositions in the '534 application and '230 patent are disclosed as essentially being growth media for stimulating growth or promoting trophism in skin cells. However, it was not recognized that using a low pH skin care composition comprising niacinamide may alleviate symptoms of psoriasis and/or atopic dermatitis, thereby improving skin barrier function and skin appearance.

Typically, cosmetic compositions are formulated to have a slightly acidic to neutral pH (i.e., from 4.0-7.0) which is believed to improve the stability of certain ingredients in the composition (e.g., niacinamide, salicylates, and neutralized thickeners). However, formulating a skin care composition at a lower pH (e.g., 1.0-4.0) may bolster the acid mantle of the skin, provide flexibility in other types of skin agents that can be included in the composition, and/or provide an exfoliation benefit. Accordingly, it would be desirable to provide a low pH skin care composition that includes niacinamide for improving skin barrier function and skin appearance.

SUMMARY

A method of treating a skin barrier condition is provided herein. The method involves identifying a target portion of skin on a person in need of treatment, and then applying a low-pH composition to the target portion of skin during a treatment period. The low-pH composition contains an effective amount of a vitamin $B_3$ compound and has a pH of less than 5.0.

BRIEF DESCRIPTION OF THE DRAWING

The FIGURE is a bar chart illustrating the synergistic effect of niacinamide and low pH on the level of normalized S100-A7 [SEQ ID NO: 2].

DETAILED DESCRIPTION

The undesirable symptoms of psoriasis and atopic dermatitis are well known. However, it has now been discovered that using niacinamide at low-pH may be useful for treating symptoms of these and other skin barrier conditions. Surprisingly, it has also been discovered that the combination of niacinamide and low pH appears to provide a synergistic reduction in S100-A7 [SEQ ID NO: 2], which is a protein believed to play an important role in causing symptoms associated psoriasis, atopic dermatitis, and other skin barrier disorders.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

SEQUENCE LISTING

A sequence listing that sets forth the nucleotide sequence for 5100 calcium binding protein A7 ("S100A7") [SEQ ID NO: 1] and protein S100-A7 [SEQ ID NO: 2] are being filed concurrently with the present application as an ASCII text file titled "15304P_seq_list_ST25". This ASCII text file was created on Jun. 26, 2018 and is approximately 4.94 KB in size. In accordance with MPEP § 605.08 and 37 CFR § 1.52(e), the subject matter in the ASCII text file is incorporated herein by reference.

DEFINITIONS

"Apply" or "application", as used in reference to a composition, means to apply or spread the compositions of the present invention onto a human skin surface such as the epidermis.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of a vitamin $B_3$ compound is an amount sufficient to improve the health and/or appearance of psoriatic skin during a treatment period. In some instances, an effective amount may be demonstrated using ex vivo and/or in vitro methods.

"Improve the appearance of" means providing a measurable, desirable change or benefit in skin appearance, which may be quantified, for example, by a decrease in redness, inflammation, and/or plaque scales.

"Low pH" means a pH of less than 5.0 (e.g., 1.5 to 5.0 (exclusive); 2.0 to 4.5, 2.5 to 4.0, or about 3.5). A suitable method of determining the pH of a composition is described in more detail below.

"Neutral pH" means a pH of 5.0 to 8.0.

"Safe and effective amount" means an effective amount of an ingredient that is low enough to avoid serious side effects (within the scope of sound medical judgment).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Synergy" and variations thereof mean a bilirubin degrading effect provided by using niacinamide in combination with a low-pH composition that is more than the predicted additive effect of the vitamin $B_3$ compound and low pH.

"Treatment period," as used herein, means the length of time and/or frequency that a material or composition is applied to a target skin surface.

"Vehicle control" means a negative control that is identical to the test composition except that it does include the particular active(s) of interest (e.g., does not contain a vitamin $B_3$ compound).

Composition

The skin care compositions herein are intended for topical application to human skin for improving the appearance and/or function of psoriatic skin. The compositions herein include an effective amount of a vitamin $B_3$ compound and have a pH of less than 5.0 (e.g., less than 4.5, 4.0, 3.5, 3.0, 2.5 or even 2.0 or less). The compositions are formed by mixing the vitamin $B_3$ compound with a dermatologically acceptable carrier, which may be done using conventional methods known to those skilled in the art. The compositions may optionally include one or more skin actives of the type commonly included in skin care compositions of the type. The compositions may be cosmetic compositions, pharmaceutical compositions, or cosmeceutical compositions, and may be provided in various product forms, including, but are not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), and the like. The composition form may follow from the particular dermatologically acceptable carrier chosen, if present in the composition.

Vitamin $B_3$ Compound

The compositions of the present invention include a safe and effective amount of a vitamin $B_3$ compound. In addition to treating one or more symptoms of psoriasis and/or atopic dermatitis, the vitamin $B_3$ compound may also be useful for regulating other skin condition, for example, as described in U.S. Pat. No. 5,939,082. The compositions herein may contain 0.01% to 15%, by weight, of the vitamin $B_3$ compound, based on the weight or volume of the composition (e.g., 0.1% to 10%, 0.1% to 3%, 0.5% to 8%, 1% to 5%, or even 2% to 4%).

As used herein, "vitamin $B_3$ compound" means a compound having the formula:

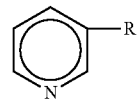

Where:
R is $CONH_2$ (i.e., niacinamide), COOH (i.e., nicotinic acid) or $CH_2OH$ (i.e., nicotinyl alcohol); derivatives thereof; and salts of any of the foregoing.

Exemplary derivatives of vitamin $B_3$ compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide.

Dermatologically Acceptable Carrier

The compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the vitamin $B_3$ compound can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 4:25 to 2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Emulsifier

When the dermatologically acceptable carrier is in the form of an emulsion, it may be desirable to include an emulsifier to provide a stable composition (e.g., does not phase separate). When included, the emulsifier may be present at an amount of 0.1% to 10% (e.g., 1% to 5%, or 2%-4%). Emulsifiers may be nonionic, anionic or cationic. Some non-limiting examples of emulsifiers that may be suitable for use herein are disclosed in U.S. Pat. Nos. 3,755,560; 4,421,769; and McCutcheon's Detergents and Emulsifiers, North American Edition, pages 317-324 (1986).

Thickeners

In some instances, it may be desirable to use thickeners that tolerate a lower range of pH. For example, neutralized thickeners may degrade at lower pH and thus may not impart the desired thickening or feel properties to the composition. On the other hand, fatty alcohol thickeners such as cetyl alcohols and stearyl alcohols are generally stable at low pH (e.g., pH of less than 5.0 or even between a pH of about 2.5 to about 4.0), and thus may be particularly suited for use in the low pH compositions herein. Accordingly, the present compositions may be free or substantially free of neutralized thickeners and/or may have from 0.1.% to 10% (e.g., from about 0.5% to about 8%, from about 1.0% to about 5%, or even from about 2% to about 4%) of a fatty alcohol thickener.

Other Optional Ingredients.

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition at low pH, especially pH sensitive ingredients like niacinamide, salicylates and peptides. In some instances, it may be desirable to select skin care actives that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Methods of Use

The low-pH compositions herein include an effective amount of a vitamin $B_3$ compound and are formulated for topical application to skin. The method involves identifying a target portion of skin on a person in need of treatment or where treatment is desired (e.g., skin that is exhibiting impaired barrier function) and applying the low-pH composition to the target portion of skin. The target portion of skin may be on a facial skin surface such as the forehead, perioral, chin, periorbital, nose, and/or cheek) or another part of the body (e.g., hands, arms, legs, back, chest). The target portion of skin may be identified according to known methods of identifying skin with impaired barrier function. For example, the target portion of skin may be identified as needing treatment if it exhibits signs of psoriasis or atopic dermatitis (redness, itchiness, painfulness, inflammation, plaques, scales, etc.). In another example, the target portion of skin may be identified as needing treatment if it exhibits a trans-epidermal water loss (TEWL) that exceeds a threshold level. In still another example, the target portion of skin may be identified as needing treatment if expression of S100A7 [SEQ ID NO: 1] is greater than a threshold value, for example, as demonstrated by a high level of S100-A7 [SEQ ID NO: 2]. In a further example, a target portion of skin may be selected that does not currently exhibit signs of reduced barrier function, but the user desires to provide a preventative benefit, especially if the target portion of skin has previously exhibited signs of reduced barrier function.

In some instances, the method of treating a skin barrier condition involves selecting an effective amount of a vitamin $B_3$ compound and a suitable pH for a skin care composition that will provide a synergistic reduction in S100-A7 [SEQ ID NO: 2]. The selected amount of vitamin $B_3$ can be combined with a dermatologically acceptable carrier to make the skin care composition at the selected pH. The resulting skin composition is then provided to person in need of treatment, for example, via a retail store or direct-to-consumer sale. In this example, the effective amount of vitamin B3 compound and/or pH of the skin composition may be selected by determining their ability to synergistically reduce S100-A7 [SEQ ID NO: 2] in at least one of an in vitro assay, ex vivo assay, of in vivo assay.

The composition may be applied locally to the target portion of skin in need of treatment and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present compositions may improve the appearance and/or barrier function of skin, for example, by reducing redness, inflammation, itchiness, pain, dry/flaky skin, trans-epidermal water loss, the size and/or number of psoriatic plaques, and/or the level of S100-A7 [SEQ ID NO: 2]).

The treatment period is ideally of sufficient time for the vitamin $B_3$ compound present in the low-pH composition to improve the appearance and/or barrier function of a target portion of skin. The treatment period typically lasts for at least 1 week (e.g., about 2 weeks, 4 weeks, 8 weeks, or even 12 weeks). In some instances, the treatment period may extend over multiple months (i.e., 3-12 months). In some instances, the composition is applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a psoriatic plaque) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

EXAMPLE

This example demonstrates the unexpected ability of a low-pH composition comprising niacinamide to potentially improve the appearance and/or barrier function of skin suffering from psoriasis, atopic dermatitis, and/or skin barrier conditions. In this example, changes in the level of S100-A7 [SEQ ID NO: 2] are used as a surrogate for the effect of the low-pH, niacinamide containing composition on skin barrier function.

Skin care agents that can downregulate S100A7 [SEQ ID NO: 1] are considered a promising approach to treating symptoms of psoriasis, atopic dermatitis, and other skin barrier conditions. S100A7 [SEQ ID NO: 1], also called psoriasin, is a member of the S100 multigene family that is encoded in the epidermal differentiation complex on chromosome Iq21. S100A7 [SEQ ID NO: 1] is highly expressed in epidermal hyperproliferative disease, and overexpression of S100A7 [SEQ ID NO: 1] is believed to contribute to the symptoms of psoriasis (Ekman, et al., "Overexpression of Psoriasin (S100A7) Contributes to Dysregulated Differentiation in Psoriasis," Acta Derm Venereol, 2017 Apr. 6, 97(4); 441-448). S100A7 [SEQ ID NO: 1] has also been reported to be upregulated in cases of atopic dermatitis and other skin barrier conditions (Glaser, et al., (2008); "The Antimicrobial Protein Psoriasin (S100A7) Is Upregulated in Atopic Dermatitis and after Experimental Skin Barrier Disruption" Journal of Investigative Dermatology, 129(3), 641-649). Thus, it is believed, without being limited by theory, that inhibiting the expression of S100A7 [SEQ ID NO: 1] and/or reducing the level of S100-A7 [SEQ ID NO: 2] will alleviate symptoms of psoriasis, atopic dermatitis, and other skin barrier conditions associated with overexpression of S100A7 [SEQ ID NO: 1] and/or accumulation of S100-A7 [SEQ ID NO: 2].

In this example, a low-pH composition (pH 2.5) comprising niacinamide at 5% (w/v) was tested to determine its ability to regulate the expression of S100A7 [SEQ ID NO:

1]. A vehicle control was used in this Example as the negative control. The expression level of S100A7 [SEQ ID NO: 1] was determined by measuring the normalized amount of protein S100-A7 [SEQ ID NO: 2] present in each sample.

Sample Prep and Test Method

Keratinocytes from human donors (available from Lonza, N.J.) are cultivated with Complete KBM Gold media until they reached 70-80% confluency. The keratinocytes are then subcultured per manufacturer's recommendations and used at either passage 1 or 2. For growth of keratinocytes on de-epidermized dermis (DED), two media are used. Medium 1 is used for the first three days while the cultures remained submerged and Medium 2 is used when cultures are raised to the air-liquid interface and then until the time of collection.

Medium 1 consists of: Dulbecco's Modified Eagle Medium (DMEM) and Ham's F-12 Nutrient Mixture at a ratio of 3:1, followed by the addition of Hyclone Cosmic Calf Serum (5%), Hydrocortisone (0.4 µg/ml), epidermal growth factor (0.02 mg/ml), transferrin (3 mg/me, insulin (5 µg/ml), cholera toxin (0.02 µg/ml), triiodothyronine ($2\times10^{-11}$ M), adenine (0.18 mM), sodium pyruvate 1×, GlutaMax 1× (Invitrogen), $CaCl_2$ (300 uM), 1× CD lipid concentrate 300 µM, fibroblast growth factor 7 (FGF-7) (10 ng/ml), and penicillin/streptomycin 1×.

Medium 2 consists of: medium 1 modified with the addition of 1% serum and removal of FGF-7 and 1 mM $CaCl_2$). Medium 1 is used for two days while the cultures remain submerged and Medium 2 is used for cultures raised to the air-liquid interface.

De-epidermized dermis (DED) is prepared by removing fat from the skin sample with a scalpel, cutting the skin into squares measuring 1.25 $cm^2$, and placing the samples in 1M NaCl plus 10× penicillin/streptomycin. The sample is incubated overnight at 37° C. The following day, the epidermis is carefully peeled off with forceps and dermal tissue is stored in phosphate-buffered saline (PBS) plus 2× penicillin/streptomycin at 4° C. until ready for use.

Approximately $5\times10^5$ keratinocytes in 50 µl of Medium 1 are pipetted into 8 mm cloning cylinders placed atop DEDs. 2 ml of Medium 1 is added to the bottom of the 6-well plate containing the transwell. The plates are incubated overnight at 33° C. in 5% $CO_2$ and 55% RH. The following day, the cloning cylinders are removed and cultures are submerged in Medium 1. At three days, cultures are raised to the air-liquid interface in Medium 2.

At day 7 at the air-liquid interface, the cultures are treated topically with one of four test compositions (a vehicle control at pH 2.5 or pH 5, or a 5% (w/v) niacinamide composition at pH 2.5 or pH 5), and one sample is left untreated, for a total of five test legs. Each test leg has four replicates. The pH of each sample can be adjusted using 1M HCl pH titration, for example, performed separately before the experiment set up to determine how much 1M HCl is needed for each leg to achieve targeting pH level. Cultures are dosed topically twice per day for 5 days. The keratinocytes are isolated from each culture on day 5 using 3.8% ammonium thiocyanate. The keratinocytes are weighed and then flash-frozen for mass spectrometry and protein level determination.

S100-A7 Protein Measurement

Frozen keratinocyte samples are thawed. 20 ul/mg (wet weight) of keratinocytes are placed in a solution of 4% sodium dodecyl sulphate, 0.1 M dithiothreitol, and 150 mM Tris (pH 7.5) and sonicated for 30 minutes to lyse the cells. Filter-aided sample preparation is used to prepare peptides for Liquid Chromatography-Mass Spec analysis. Lysate prepared above is centrifuged for 10 minutes at 18,000×g to clarify, and the supernatant is then mixed in a 1:10 ratio with 180 µl 8M Urea, 150 mM Tris (pH 8.5). This mixture is placed into YM-30 centrifugal filter unit (Millipore) and centrifuged for 10 minutes at 14,000×g. Proteins are captured on the filter. We then add 200 µl 8M Urea, 150 mM Tris pH 8.5 to the filter and spin as above to wash. 100 µl 50 mM iodoacetamide is added to the filter and incubated for 30 minutes at ambient temperature in the dark to alkylate cysteine residues. This buffer is then centrifuged through the filter and followed with 3 wash steps of 200 µl 8M Urea, 150 mM Tris pH 8.5 as above. This is followed by 3 wash steps of 200 µl 100 mM Ammonium bicarbonate. 40 µl of 0.5 µg/µl Trypsin/LysC (Promega) in 100 mM Ammonium bicarbonate is added to the filter. Filter units are then incubated 16 hours in a 37° C. incubator. Resulting peptides are collected in clean tubes by centrifugation as above. Synthetic isotopically labeled internal standards (e.g., from New England Peptide) are added in equal amounts to each sample. These standards include the peptide sequence GTNYLADVFEK, with the C-terminal lysine labeled using 13C(6)15N(2). Peptides are analyzed using an Agilent 1690 Infinity LC system coupled to an Agilent 6490 QQQ mass spectrometer (or equivalent) against a scheduled multiple reaction monitoring method. Peptides are loaded onto an Agilent Zorbax RRHD Eclipse Plus 95 Å C18, 2.1×150 mm, 1.8 µm, 1200 bar column heated to 50° C. Mobile phases are A: 0.1% Formic acid in water and B: 0.1% Formic Acid, 90% Acetonitrile, 9.9% water. The flow rate is 0.4 ml/min. The dynamic MRM method contains 4 transitions for the GTNYLADVFEK peptide. These transitions are based on the doubly-charged precursor 628.8115 m/z for the endogenous peptide and 632.8186 m/z for the labeled internal standard. Peaks are manually verified using the Skyline software and peak areas are exported for further normalization and analysis.

The results of the test are summarized below in Table 1. The protein values shown are the averaged amount of S100-A7 [SEQ ID NO: 2] detected for the 4 replicates in each test leg. The measured protein amount is the log 2 normalized intensity after fitting nonlinear regression models using the default settings for the MSstats statistical analysis package. The delta versus untreated value is calculated by subtracting the measured protein amount for each leg from the measured protein amount for the untreated leg. The normalized protein amount reflects the amount of measured S100-A7 normalized to the untreated sample, which is assigned a baseline value of 100. The p-value is determined by combined pairwise ANOVA comparison of the experimental conditions corrected for multiple hypothesis testing using the Benjamini & Hochberg method. A p-value of 0.1 or less is considered statistically significant.

TABLE 1

| Sample | Measured protein (log2) | Δ vs. Untreated | Normalized protein | p-value |
|---|---|---|---|---|
| Untreated | 18.75 | 0 | 100 | |
| Vehicle pH 2.5 | 17.8 | 0.95 | 51.8 | 0.2057 |
| Vehicle pH 5 | 17.6 | 1.15 | 45 | 0.0496 |
| 5% Niacinamide at pH 2.5 | 15.5 | 3.25 | 10.5 | <0.0001 |
| 5% Niacinamide at pH 5 | 17.5 | 1.25 | 42 | 0.0613 |

Table 2 and FIG. 1, illustrate the unexpected reduction in S100-A7 [SEQ ID NO: 2] caused by the low-pH, 5% niacinamide composition. The protein amounts provided in Table 2 are based on the normalized protein amounts from Table 1. As can be seen in Table 2 and FIG. 1, lowering the pH of the vehicle control does not result in a statistically significant change in protein level. The 5% niacinamide composition also appears to have no significant effect on protein level at neutral pH. Based on the observed individual effects of low pH and niacinamide at neutral pH, it would be expected that the combined effect would not significantly affect the level of S100-A7 [SEQ ID NO: 2]. However, the observed effect of using niacinamide in a low-pH composition surprisingly resulted in a significant change in the level of S100-A7 [SEQ ID NO: 2]. Thus, providing a low-pH skin care composition that includes a vitamin $B_3$ compound such as niacinamide may provide a better way to treat skin barrier conditions related to an overexpression of S100A7 [SEQ ID NO: 1].

TABLE 2

| Test Leg Comparison | Δ Normalized Protein | p-value |
|---|---|---|
| A. Effect of Niacinamide (Vehicle pH 5 - 5% Niacinamide pH 5) | 3 | 0.9823 |
| B. Effect of low pH (Vehicle pH 5 - Vehicle pH 2.5) | −6.8 | 0.8789 |
| C. Observed effect of low pH + Niacinamide | 34.5 | <0.0005 |
| D. Expected effect of low pH + 5% Niacinamide (A + B) | −3.8 | 0.7011 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating psoriasis or atopic dermatitis, comprising:
   a) identifying a target portion of skin on a person exhibiting a symptom of psoriasis or atopic dermatitis; and
   b) applying a low-pH composition to the target portion of skin during a treatment period, wherein the low-pH composition comprises an effective amount of niacinamide, has a pH of about 2.5, and reduces the amount of S100-A7 [SEQ ID NO: 2] according to the S100-A7 Protein Measurement method.

2. The method of claim 1, wherein the composition comprises about 0.01% to about 10% of niacinamide.

3. The method of claim 1, wherein the composition downregulates S100A7 [SEQ ID NO: 1] relative to a control.

4. The method of claim 1 wherein the reduction in S100-A7 [SEQ ID NO: 2] is at least 10% more than a predicted additive amount of S100-A7 [SEQ ID NO: 2] reduction.

5. The method of claim 1, wherein the composition comprises at least one additional skin care active selected from the group consisting of vitamins, minerals, peptides, sugar amines, sunscreens, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, and combinations thereof.

6. The method of claim 1, wherein the composition comprises about 0.1% to about 10% of a stable fatty alcohol thickener.

7. The method of claim 6, wherein the stable fatty alcohol thickener is selected from the group consisting of cetyl alcohols, stearyl alcohols, and combinations thereof.

8. A method of treating psoriasis or atopic dermatitis, comprising:
   a) determining an effective amount of niacinamide and a pH for providing a reduction in the expression of S100 calcium binding protein A7 [SEQ ID NO: 1] by contacting keratinocytes with a composition comprising niacinamide and having a pH of about 2.5, and measuring the change in the amount of S100-A7 [SEQ ID NO: 2];
   b) combining the effectives amount of niacinamide with a dermatologically acceptable carrier to make a skin care composition at the determined pH;
   c) providing the skin care composition to a person exhibiting a symptom of psoriasis or atopic dermatitis; and
   d) applying the composition to a portion of skin exhibiting the symptom of psoriasis or atopic dermatitis.

9. The method of claim 8, wherein the effective amount of niacinamide is between 0.01% and 10%, by weight of the composition.

10. The method of claim 8, wherein the skin care composition comprises at least one additional skin care active.

11. The method of claim 8, wherein the composition reduces the S100-A7 level by at least 10% compared to a corresponding neutral pH composition.

12. The method of claim 1, wherein the low-pH composition is free of neutralized thickeners.

\* \* \* \* \*